United States Patent [19]

Griffith et al.

[11] 4,356,296

[45] Oct. 26, 1982

[54] FLUORINATED DIACRYLIC ESTERS AND POLYMERS THEREFROM

[75] Inventors: James R. Griffith, Riverdale; Jacques G. O'Rear, Temple Hills, both of Md.

[73] Assignee: The United States of America as represented by the Secretary of the Navy, Washington, D.C.

[21] Appl. No.: 237,838

[22] Filed: Feb. 25, 1981

[51] Int. Cl.³ .............................................. C08F 14/18
[52] U.S. Cl. ............................... 526/242; 204/159.23; 560/219; 560/221
[58] Field of Search .................... 526/242, 323.1, 323.2

[56] References Cited

U.S. PATENT DOCUMENTS 2,830,078  4/1958  Fekete ............................... 526/323.1

Primary Examiner—Harry Wong, Jr.
Attorney, Agent, or Firm—Robert F. Beers; William T. Ellis; Thomas E. McDonnell

[57] ABSTRACT

A diacrylate monomer represented by the formula:

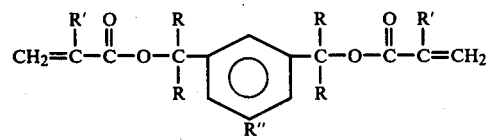

wherein R represent $CF_3$ or $C_2F_5$, R' represents —H or —$CH_3$, R" represents H or —$(CF_2)_nF$, and n is an integer from 1 to 10, and polymer therefrom.

10 Claims, No Drawings

FLUORINATED DIACRYLIC ESTERS AND POLYMERS THEREFROM

BACKGROUND OF THE INVENTION

The present invention pertains generally to fluoropolymers and in particular to fluorinated acrylic polymers.

Acrylic polymers, whether linear or cross-linked, are excellent adhesives. They can be easily fabricated into many different components and shapes. Acrylics have exceptional optical clarity, strength, and dimensional and color stability. They have a convenient liquid-to-solid transistion upon curing and can be cured by radiation.

Fluorocarbons have a much broader resistance to physical and chemical attack than acrylic polymers, but lack the advantages of acrylic polymers. This suggests that acrylics can be enhanced by the introduction into the molecules of substantial amounts of fluorine, provided such an addition does not compromise the characteristic acrylic properties. Fluorocarbons also possess a range of unusual surface chemical properties which would increase the versatility of acrylics if combined with them. For example, in the liquid precured state, of a fluoroacrylic resin is expected to have a low surface tension and excellent wetting capability for difficult-to-wet fillers, such as powdered Teflon, whereas the cured fluoroacrylic can be expected to be relatively non-wetting and non-absorptive of most liquid systems, particularly those that are water based.

The problem of introducing substituted quantities of stable fluorocarbon into resins without undue compromise of the strength properties has been previously solved for epoxy systems by utilizing, as intermediates, a series of fluorinated tertiary alcohols with an aromatic nucleus surrounded by perfluorinated aliphatic groups and bearing hydroxyl functionalities derived from hexafluoroacetone as intermediates. Examples of this technique are reported in (1) J. G. O'Rear et al., Journal of Paint Technology, 43(552); p. 113, 1970; (2) J. R. Griffith et al., Synthesis, 1974(1); p. 493; and (3) D. L. Hunston et al., Ind. Eng. Chem. Prod. Res. Dev., 17(1): p. 10 (1978).

Attempts to esterify these intermediates directly by the use of acrylic acid or acrylic anhydride have not been successful. A cis-trans fluoropolyol acrylic resin has however been prepared by a method comprising reacting a cis-trans diol derived from hexafluoroacetone and propene, a fluoroaromatic diol, and epichlorohydrin in refluxing acetone with a 10% excess of aqueous sodium hydroxide to produce a fluoropolyol monomer, reacting the fluoropolyol monomer with acrylic acid anhydride, purifying the ester by percolating its ether solution through alumina, and polymerizing the ester. This method is disclosed in U.S. Pat. No. 4,284,747 issued on Aug. 18, 1981 on U.S. patent application, Ser. No. 124,203, by J. R. Griffith and J. G. O'Rear, filed on Feb. 25, 1980. The disadvantage with this acrylic resin is the limitation on the number and length of the pendant perfluoroalkyl groups.

Fluorinated acrylic polymers have been prepared from fluorinated monoacrylate monomers. One polymer of note is from phenylbis(trifluoromethyl)carbinyl acrylate, reported in J. N. Roitman and A. G. Pittman, Jr. Polym. Sci., 12, 1421–1428 (1974). This monomer was prepared by reacting phenylbis(trifluoromethyl)carbinol and acryloyl chloride in tetrahydrofuran with potassium being added to form a salt with the acid byproduct. This method developed from an earlier work reported in J. N. Roitman and A. G. Pittman, J. Polym. Sci., B, 10, 449 @ 501, (1972) in which fluorinated monoacrylate monomers are prepared by reacting a fluorinated alcohol with acryloyl chloride in 1,1,2-trifluro-1,2,2-trichloroethane with triethylamine being added as an acid acceptor. Fluorinated diacrylate monomers cannot be prepared by the first of these methods because the solvents cannot prevent phase separation. Further, both methods use vacuum distillation to purify the product which cannot be used to purify higher-boiling diacrylate monomers due to the fast polymerization of these monomers, even under a vacuum. The addition of polymerization inhibitors would require a much higher distillation temperature which would in turn nullify the effect of the inhibitors.

Diacrylate monomers are important because their polymerization produces three-dimensional network polymers which are thermosets. In contrast, monoacrylate polymers are thermoplastic, a property detrimental to most high-temperature applications.

SUMMARY OF THE INVENTION

It is, therefore, an object of the present invention to substantially increase the fluorocarbon content in acrylic resins, without interfering with the acrylate properties.

Another object of this invention is to vary the fluorine content of fluroacrylic resins over wide ranges through the placement of perfluoroalkyl pendant groups of different lengths.

These and other objects are achieved by reacting a fluoroaromatic diol and acryloyl chloride in a highly fluorinated solvent with an acid acceptor to form a fluorinated diacrylate ester monomer and purifying the monomer by forming a solution, adding decolorizing carbon to the solution and percolating the solution through activated alumina.

DETAILED DESCRIPTION OF THE INVENTION

The fluorinated diacrylate monomers of the present invention are represented by the formula:

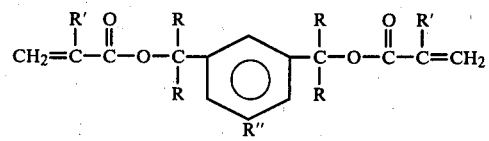

wherein R represents $-CF_3$ or $-C_2F_5$, R' represents $-H$ or $-CH_3$, R" represents H, or $-(CF_2)_nF$, and n is an integer from 1 to 10. Due to the availability and relatively low cost of fluoroacetone, a starting material for R representing $-CF_3$, the most preferred R is $-CF_3$. Another excellent monomer has each carbon atom to which the "R" groups are attached having a different fluoroalkyl group. This monomer would be prepared from perfluoromethyl ethyl ketone. The preferred values for n is from 3 to 7 and the most preferred values for n are 3,5, and 7. The dimethacrylate monomers (R' representing $-CH_3$) has a melting point about 40° C. lower than monomers with H— as R'. Thus the monomer with a lower melting point would have many processing advantages over monomers with higher melting points.

The diacrylate monomers of this invention are prepared by reacting a 1,3 bishydroxyperfluoroalkyl benzene with acrylyl chloride in a highly fluorinated fluorocarbon solvent (one with at least 50 percent fluorine substituted) in the presence of a tertiary amine acid acceptor. The preferred solvents are trifluorotrichloroethane (especially 1,1,2-trifluoro-1,2,2-trichloroethane), Freon 113, tetrafluoroethane, and tetrafluoropropane. The preferred acid acceptor is triethylamine. Preferably acrylylchloride is reacted in a 0.5 to 1.0 percent stoichiometric excess and the amount of solvent is at least sufficient to dissolve the reactants but not more than a 50 percent excess. The acid acceptor is also preferably added in a 0.5 to 1.0 percent stoichiometric excess. It is also preferred that the reaction temperature is from 5° to 20° C.

Triethylammonium hydrochloride is a by-product which precipitates out and can be removed by, e.g., filtering. Its removal facilitates purification of the monomer to a useful degree of purity.

The monomer is purified by the method comprising dissolving the crude monomer containing minor amounts of unreacted diol and monoester in a solvent. Preferably the solvent is Freon 113 or ether. The solution is clarified with preferably decolorizing carbon and percolated through activated alumina.

The diacrylate ester is easily polymerized by a free radical catalyst or u.v. radiation. Raising the temperatures above the melting point of the monomer also causes polymerization. The resulting polymers are infinite-molecular-weight polymers, making a precise molecular weight determination impossible.

To better demonstrate the advantages of the present invention the following examples are given. It is understood that these examples are given by way of illustration and are not intended to limit the disclosure or the claims to follow in any manner.

EXAMPLE I 1,3-Bis(2-hydroxyhexafluoro-2-propyl)benzene diacrylate, I

A solution of 1,3-bis(2-hydroxyhexafluoro-2-propyl)benzene (139.4 g, 0.34 mole) in Freon 113 (350 ml) was stirred magnetically in a 3-neck flask (1,000 ml) equipped with a dropping funnel, thermometer, dry-ice condenser and drying tube (calcium chloride). Triethylamine (69.0 g, 0.68 mole) in Freon 113 (40 ml) was added dropwise during 20 minute (exotherm: 25° to 40° C.). At this point an external cooling bath (ice-water) was applied. Then a second dropping funnel charged with acryloyl chloride (61.5 g, 0.68 mole) in Freon 113 (40 ml) was quickly substituted in the place of the empty dropping funnel. A cautious addition of the latter was completed in 75 minutes with stirring at 10° to 20° C. After 2 hours of additional stirring, the resulting white slurry was vacuum-filtered (350 ml coarse fritted glass filter packed with 10 g of Celite) and washed with Freon 113 (50 ml) to remove the precipitate. Flash evaporation of the straw-colored filtrate resulted in 157.1 g of yellow oil, assaying 1.2 wt. percent of the starting diol, 3.4 wt. percent of the monoester and 94.6 wt. percent of the diester. The yellow oil was dissolved in Freon 113 (1,000 ml), the resulting solution agitated with a mixture of Nuchar (25 g) and Celite (25 g), the latter filtered through packed Celite (30 g) and washed with Freon 113 (500 ml). The clarified filtrate was percolated and washed successively through two chromatographic columns (73 mm OD×30 cm). Both were fitted with a coarse fritted glass disc, charged with Woelm neutral activated alumina (140 g), packed Celite (40 g) and glass wool (1 g). Flash evaporation of the effluent (finally at 40°/2 mm) left 112.2 g (63.7% yield) of analytical I (100% purity by GLC) as white, almost odorless crystals; mp 65°–68° C.,

EXAMPLE II 1,3-Bis(2-hydroxyhexafluoro-2-propyl)-5-heptafluoropropylbenzene diacrylate, II. Reaction of 1,3-bis(2-hydroxyhexafluoro-2-propyl)-5-heptafluoropropylbenzene (11.56 g, 0.020 mole) with triethylamine (4.09 g, 0.040 mole), followed by reaction with acryloyl chloride (3.63 g, 0.040 mole), was performed in the customary manner. Filtration left a straw-colored filtrate, found by evaporation of an aliquot to contain 0.2% starting diol, 2.1% monoester and 97.5% II. Customary decolorizing and column chromatography yielded 10.0 g (72.9% yield) of analytical II (100% by GLC) as white, almost odorless crystals; mp 57°–59° C.; $n_D^{60}$ 1.3684.

EXAMPLE III 1,3-Bis(2-hydroxyhexafluoro-2-propyl)-5-pentadecafluoroheptylbezene diacrylate, III. Triethylamine (1.60 g, 0.0158 mole) was added to 1,3-bis(2-hydroxyheptafluoro-2-propyl)-5-pentadecafluoroheptylbenzene (5.00 g, 0.00643 mole) and then reacted with acryloyl chloride (1.39 g, 0.0154 mole) in the ordinary manner. Work-up of the filtrate gave 5.69 g of cream-colored crystals analyzing 0.6% starting diol, 6.0% monoester and 93.4% III. Customary purification steps led to 3.8 g (66.7% yield) of analytical III (>99.95% by GCL) as a clear, viscous oil which crystallized overnight to yield white, almost odorless crystals; mp 35°–37° C.; $n_D^{25}$ 1.3710 (supercooled).

EXAMPLE IV

Samples of Examples I to III were mixed with 2,2'-azobis(2-methylpropionitrile) and were heated to 50° C. Polymerization occurred quickly.

EXAMPLE V

Other samples of Examples I to III were mixed with benzoin ethers, heated to 25° C., and irradiated with ultraviolet light. The irradiation times were 20 to 30 seconds in duration. Polymerization occurred quickly.

These examples are reported in James R. Griffith and Jacques G. O'Rear, *Org. Coat. and Plast. Chem., Preprints*, Vol. 42, p. 204, March 1980, which is incorporated herein by reference.

Since most of the fluoromonomers are solids at room temperature which have strong crystallizing tendencies, it is convenient to dissolve the solids in liquid fluorinated monoacrylate I at moderately elevated temperatures and effect the polymerization before crystallization can occur.

Several of the highly fluorinated diacrylate monomers readily wet powdered Teflon, and the cured compositions have a white, semitranslucent appearance which closely approximates that of attractive teeth. The compositions are extremely hydrophobic, and if polished before measurements are made, have static and kinetic friction coefficients of 0.15 and 0.14, respectively, which are between those of polytetrafluoroethylene and tetrafluoroethylene-hexafluoropropylene copolymer. In addition to possible dental applications, these properties suggest such uses as artificial hip ball and socket prostheses in which the acrylic matrix would provide moldability and structural strength, including coldflow resistance, and the Teflon dispersed phase would provide permanent lubricity to the moving faces. Although not yet proven conclusively, it is reasonable to expect that these compositions would be highly impervious to body fluids, including saliva, and resistant to staining. The fluoroacrylic materials appear to be particularly promising for dental and biomedical applications. However, all of the other acrylic uses, such as coatings, castings, encapsulants, caulks, etc., based upon linear or three-dimensional polymers can also be realized. The special properties imparted by the presence of fluorocarbon should make these substances uniquely applicable for many purposes.

To those skilled in the art, many modifications and variations of the present invention are possible in light of the above teachings. It is therefore to be understood that the present invention may be practiced otherwise than as specifically described herein and still be within the spirit and scope of the appended claims.

We claim:

1. The polymer obtained from polymerizing a fluorodiacrylic ester represented by the formula:

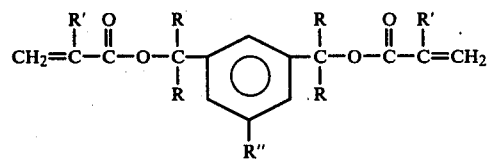

where R represents $-CF_3$ or $-C_2F_5$, R' represents $-H$ or $-CH_3$, R" represents $-H$ or $-(CF_2)_nR$, and n is an integer from 1 to 10.

2. The polymer of claim 1 wherein R' represents $-H$.

3. The polymer of claim 1 wherein n is an integer from 3 to 7.

4. The polymer of claim 3 wherein n represents 3.

5. The polymer of claim 3 wherein n represents 5 or 7.

6. The polymer of claim 3 wherein R' represents $-CH_3$.

7. The polymer of claim 6 wherein R represents $-CF_3$.

8. The polymer of claim 7 wherein n represents 3, 5, or 7.

9. The polymer of claim 2 wherein n is an integer from 3 to 7 and R represents $-C_2F_5$.

10. The polymer of claim 9 wherein n is 3, 5, or 7.

* * * * *